United States Patent
Datta

(10) Patent No.: US 10,143,848 B2
(45) Date of Patent: Dec. 4, 2018

(54) NEUROLOGICAL STIMULATOR METHOD WITH DETACHABLE LEAD CONNECTION ARRANGEMENT

(71) Applicant: Devin Datta, Merritt Island, FL (US)

(72) Inventor: Devin Datta, Merritt Island, FL (US)

( * ) Notice: Subject to any disclaimer, the term of this patent is extended or adjusted under 35 U.S.C. 154(b) by 0 days.

(21) Appl. No.: 15/283,844

(22) Filed: Oct. 3, 2016

(65) Prior Publication Data

US 2017/0021180 A1    Jan. 26, 2017

Related U.S. Application Data

(62) Division of application No. 14/532,296, filed on Nov. 4, 2014, now abandoned.

(Continued)

(51) Int. Cl.
*A61N 1/00* (2006.01)
*A61N 1/375* (2006.01)
(Continued)

(52) U.S. Cl.
CPC ......... *A61N 1/3752* (2013.01); *A61N 1/0504* (2013.01); *A61N 1/0558* (2013.01);
(Continued)

(58) Field of Classification Search
CPC .. A61N 1/0504; A61N 1/0558; A61N 1/0595; A61N 1/36017; A61N 1/36071;
(Continued)

(56) References Cited

U.S. PATENT DOCUMENTS 6,609,029 B1   8/2003   Mann et al.
8,521,290 B2   8/2013   North
(Continued)

FOREIGN PATENT DOCUMENTS

WO   2007-149936   12/2007

OTHER PUBLICATIONS

"Neurostimulation Therapy for Chronic Pain—Percutaneous Lead Implantation Guide" Medtronic, Inc: 2008; 91 pgs.
Medtronic for Healthcare Porfessionals "Spinal Cord Stimulation" http://professional.medtronic.com/pt/neuro/scs/prod/index.htm?cmpid=url_neuro_hcp_youtube_procedurevideosscs&1#tabs-: 3 pgs. Retrieved from internet Nov. 14, 2014.
(Continued)

*Primary Examiner* — Mallika D Fairchild
(74) *Attorney, Agent, or Firm* — Allen, Dyer, Doppelt + Gilchrist, PA

(57) ABSTRACT

A method may include, using an electrode lead(s) having a proximal end and a distal end and comprising spaced apart electrodes carried by the distal end, positioning the electrodes adjacent nerves in a patient; using a subcutaneous lead connector plug comprising a housing electrically connected to the proximal end of the electrode lead(s) and defining a lead connection port(s) and an anchor point(s), positioning the housing along with the proximal end of the electrode lead(s) inside the patient; connecting the anchor point(s) to tissue beneath the patient's skin and, using a first generator lead having a distal end and a proximal end, plugging the distal end of the first generator lead into the lead connector port(s); and connecting the proximal end of the first generator lead to a first neural stimulation generator, and operating the first neural stimulation generator to provide electrical stimulation to the nerves via the electrodes.

18 Claims, 6 Drawing Sheets

Related U.S. Application Data

(60) Provisional application No. 61/899,531, filed on Nov. 4, 2013.

(51) Int. Cl.
*A61N 1/05* (2006.01)
*A61N 1/36* (2006.01)
*H01R 24/58* (2011.01)

(52) U.S. Cl.
CPC ..... *A61N 1/36017* (2013.01); *A61N 1/36071* (2013.01); *H01R 24/58* (2013.01); *H01R 2201/12* (2013.01)

(58) Field of Classification Search
CPC .. A61N 1/3752; A61N 1/375; H01R 2201/12; H01R 24/58
See application file for complete search history.

(56) References Cited

U.S. PATENT DOCUMENTS

| | | |
|---|---|---|
| 8,655,455 B2 | 2/2014 | Mann et al. |
| 2003/0069623 A1 | 4/2003 | Stypulkowski |
| 2006/0195152 A1* | 8/2006 | Gerber ............... A61N 1/08 607/40 |
| 2007/0038263 A1 | 2/2007 | McIntyre |
| 2007/0179559 A1* | 8/2007 | Giftakis ............ A61N 1/36071 607/46 |
| 2011/0093034 A1 | 4/2011 | Kast et al. |
| 2012/0259386 A1 | 10/2012 | Derohan et al. |

OTHER PUBLICATIONS http://stimwave.com/products/freedom-4-scs-system; 6 pgs. Retrieved from internet on Mar. 9, 2015.

* cited by examiner

NEUROLOGICAL STIMULATOR METHOD WITH DETACHABLE LEAD CONNECTION ARRANGEMENT

CROSS-REFERENCE TO RELATED APPLICATIONS

This application is a divisional application of U.S. patent application Ser. No. 14/532,296 filed Nov. 4, 2014, which claims the benefit of U.S. Provisional App. No. 61/899,531, filed Nov. 4, 2013, the entire contents of which are hereby incorporated herein by reference.

TECHNICAL FIELD

The present disclosure generally relates to medical devices and methods, and, more particularly, to a method and system for musculoskeletal pain management.

BACKGROUND

Spinal cord stimulators are devices that are placed into the epidural space of the spinal canal and are designed to apply electrical stimulation to the dorsal column of the spinal cord (e.g., between T7-T12) to modify the pain responses from the back and legs to the brain. The epidural lead is connected to a battery/generator, usually implanted down in the patient's buttock area. In patients with chronic back and/or leg pain, these devices can provide significant pain relief and improvement in quality of life.

Currently the standard of care for using spinal cord stimulators to treat back and/or leg pain requires a percutaneous trial of the device for 4-7 days to see if the spinal cord stimulator gives adequate coverage and relief of the patient's pain. If the trial is successful, a permanent epidural lead is placed.

There are typically two options for permanent placement. With the first option, one or two leads may be placed percutaneously as in the trial using a large spinal needle to introduce the lead into the epidural space. The lead is then anchored down with a suture to the muscle fascia and then tunneled to the generator. While this is relatively less invasive and may be performed by the pain management physician without a surgeon, it may be disadvantageous in that with only 1 or 2 leads it is often difficult to find the same coverage as in the trial, possibly due to secondary scarring from the trial.

As for the second option, placement of a "paddle" lead is performed by surgically opening the spinal canal with a hemi-laminectomy and placing a wider lead with 2-5 rows of leads. A potential advantage of this approach is that with the extra leads each having several contacts, the likelihood of finding good coverage of the patient's pain is improved. However, this requires a spine surgeon to open the spinal canal and place the lead. This technique may also be utilized if the percutaneous permanent placement is not working as well as the trial.

As a result, it may be desirable to provide further improvements to spinal cord stimulator systems and associated methods for the implantation thereof which may provide higher success rates for percutaneous placement to help avoid more traumatic or invasive lead placement procedures.

SUMMARY

A neural stimulation method may include, using at least one electrode lead having a proximal end and a distal end and comprising a plurality of spaced apart electrodes carried by the distal end, positioning the distal end of the at least one electrode lead so that the electrodes are adjacent at least one nerve in a patient. Furthermore, using a subcutaneous lead connector plug comprising a housing electrically connected to the proximal end of the at least one electrode lead and defining at least one lead connection port and at least one anchor point carried by the housing, the method may further include positioning the housing along with the proximal end of the at least one electrode lead inside the patient beneath the patient's skin, and connecting the at least one anchor point to tissue beneath the patient's skin. Using a first generator lead having a distal end and a proximal end, the method may also include plugging the distal end of the first generator lead into the at least one lead connector port to electrically connect the distal end of the second lead with the at least one lead connector port. The method may further include connecting the proximal end of the first generator lead to an external neural stimulation generator outside of the patient's body, and operating the first neural stimulation generator during a trial period to provide electrical stimulation to the at least one nerve via the plurality of electrodes. In addition, the method may also include unplugging the distal end of the first generator lead from the at least one lead connector port after the trial period while leaving the at least one electrode lead and the subcutaneous lead connector plug inside the patient.

More particularly, the method may further include, after the trial period: plugging a distal end of a second generator lead into the at least one lead connector port to provide an electrical connection therewith; electrically connecting a proximal end of the second generator lead to an internal neural stimulation generator; and implanting the second generator lead and the internal neural stimulation generator inside of the patient's body so that the internal neural stimulation generator provides electrical stimulation to the at least one nerve via the plurality of electrodes during an extended use period. Moreover, the at least one lead connection port may comprise a respective lead connection port for the proximal end of the at least one electrode lead, and for the distal ends of the first and second generator leads. As such, the method may also include plugging the proximal end of the at least one electrode lead into its respective lead connection port to provide an electrical connection therewith.

In accordance with one example implementation, the at least one electrode lead and the subcutaneous lead connector plug may be integrally formed. Furthermore, the at least one electrode lead may comprise a pair of electrode leads. In addition, the at least one anchor point may comprise at least one anchor loop carried by the housing, and connecting the at least one anchor point may include connecting the at least one anchor point to tissue beneath the patient's skin.

The at least one anchor point may comprise a plurality of anchor points spaced apart along the housing in accordance with one example implementation. Further, positioning the distal end of the at least one electrode lead may comprise inserting the distal end of the at least one electrode lead percutaneously. In accordance with an example embodiment, the at least one lead connection port may comprise at least one female lead connection port, and the distal end of the at least one generator lead may define a corresponding male connection plug for the at least one female lead connection port. Furthermore, the subcutaneous lead connector plug may further include at least one set screw carried by the housing, and the method may also include securing the distal end of the at least one generator lead within the at least one lead connector port using the at least one set screw.

DETAILED DESCRIPTION

Figure 1:
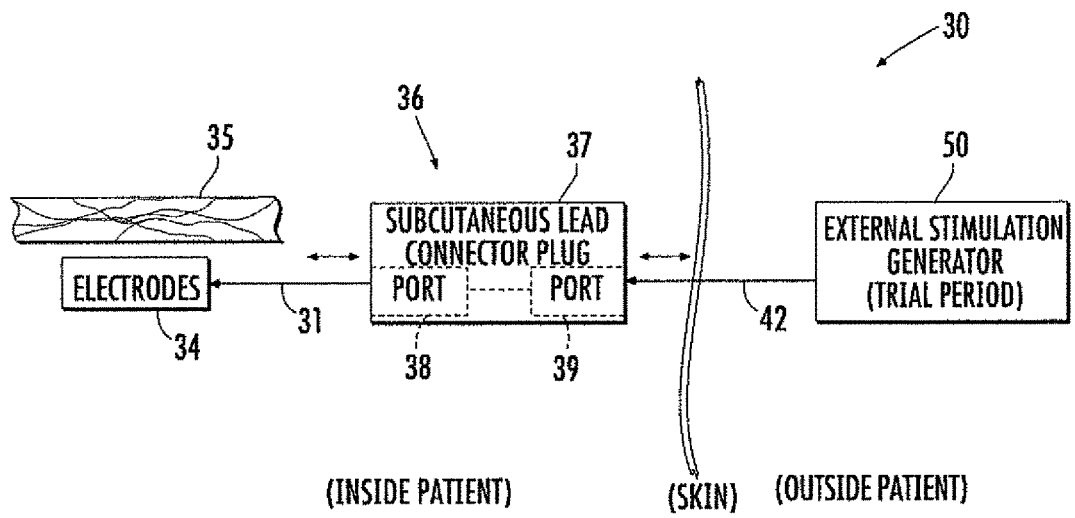
FIG. 1 is a schematic diagram of a neural stimulation system in accordance with an example embodiment during a patient trial period.
Figure 2:
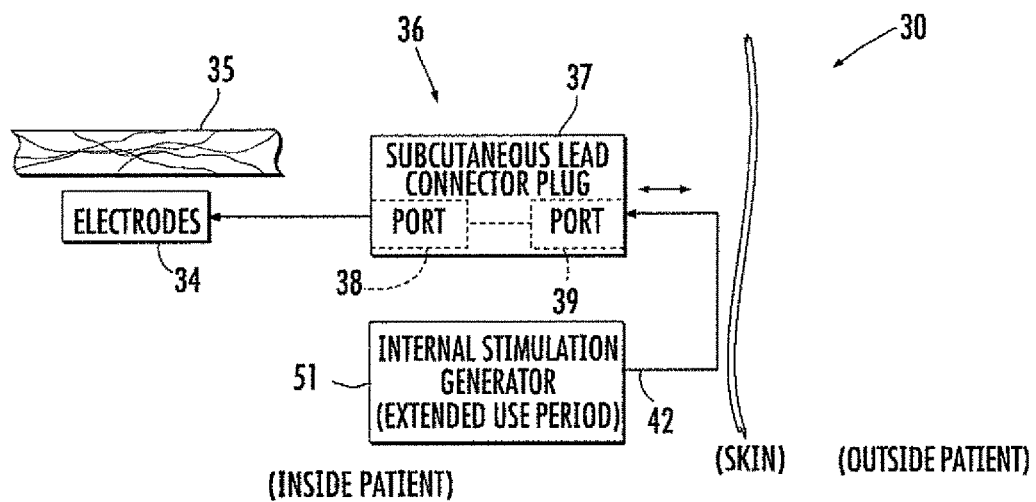
FIG. 2 is a schematic diagram of the neural stimulation system of FIG. 1 which has been converted for permanent after the trial period, in which the original electrode lead used in the trial period remains in the patient.
Figure 3:
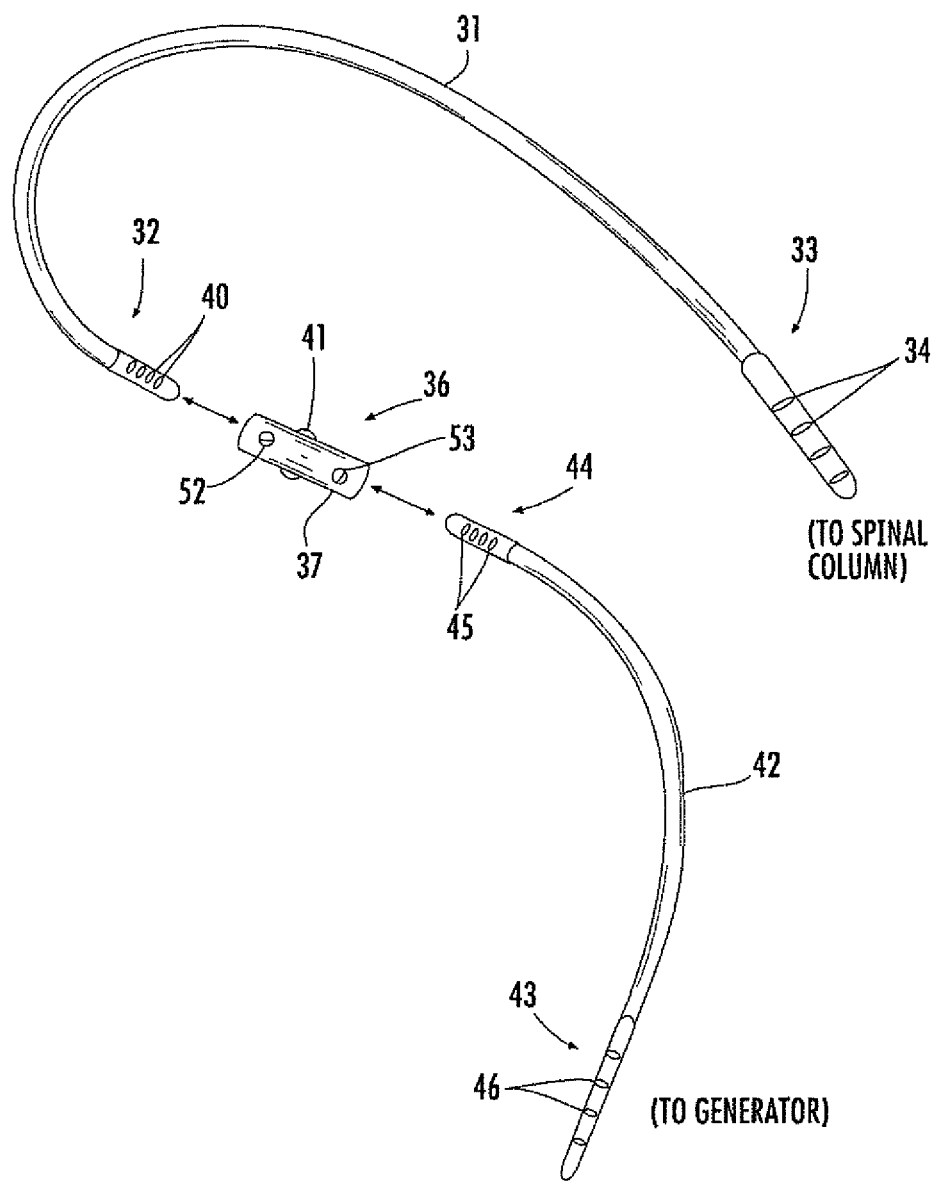
FIGS. 3 and 4 are lead and connector arrangements in accordance with an example embodiment for use with the system of FIG. 1 before and after installation, respectively.
Figure 4:
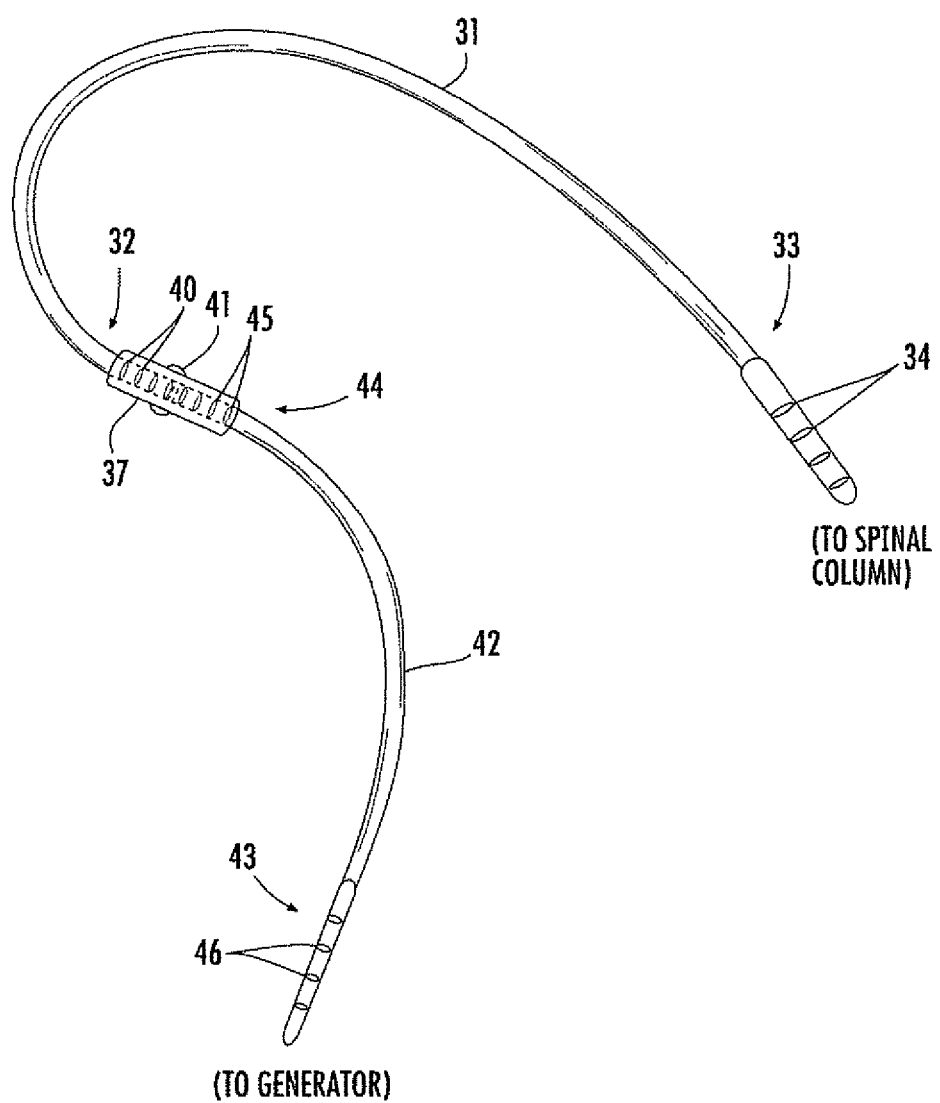

The present description is made with reference to the accompanying drawings, in which exemplary embodiments are shown. However, many different embodiments may be used, and thus the description should not be construed as limited to the embodiments set forth herein. Rather, these embodiments are provided so that this disclosure will be thorough and complete. Like numbers refer to like elements throughout, and prime notation is used to indicate similar elements in different embodiments.

With respect to neural stimulator devices, there currently is a relatively new technology that is MRI compatible, but only for percutaneous leads. This may result in an increase in the use of percutaneous trial lead placement. Yet, a potential problem with treating patients with spinal cord stimulation is having a successful trial, but when the permanent leads are placed not being able to get the same good coverage (i.e., pain relief) as the patient received in the trial period. Also, placing the leads percutaneously a second time may be more difficult because of scarring after the trial. As such, the configurations described herein advantageously allows for the initial percutaneous "trial" electrode lead to also be used as a "permanent" lead, without having to perform a second electrode lead installation procedure.

More particularly, various approaches are presented herein to perform a trial electrode lead(s) implantation, and when the trial is finished use the same well-placed electrode lead(s) to connect to a neural stimulation generator device for permanent or extended use. That is, the spinal cord stimulator converter approaches set forth herein may address the above-noted problems without having to create a "second pocket" for a secondary lead connector, as may be the case with typical approaches.

Referring initially to FIGS. 1-4, a neural stimulation system 30 illustratively includes one or more electrode leads 31 having a proximal end 32 and a distal end 33, with a plurality of spaced apart electrodes 34 carried by the distal end to be positioned adjacent one or more nerves 35 in a patient. By way of example, the nerves 35 may be the spinal cord in a spinal cord stimulation (SCS) embodiment, which will be used herein for purposes of describing the various configurations. However, the neural stimulation system 30 and associated methods described herein may also be used for other neural stimulation applications, such as deep-brain stimulation, as well as stimulation of the heart, peripheral nerves, and other body organs or tissue, as will be appreciated by those skilled in the art. Moreover, while the techniques described herein are presented with reference to a human patient, it should be noted that the system 30 and associated techniques may also be used for veterinary applications in some instances (i.e., for animal "patients").

The system 30 further illustratively includes a subcutaneous lead connector plug 36 including a housing 37 electrically connected to the proximal end 32 of the electrode lead 31. The subcutaneous lead connector plug 36 is to be positioned by a pain management physician/practitioner or surgeon along with the electrode lead 31 inside the patient beneath the patient's skin, as seen in FIG. 1. More particularly, in the illustrated example the housing 37 defines two female electrical connection ports 38, 39 on opposing ends thereof. The proximal end 32 of the electrode lead 31 is configured as a male plug with electrical contacts 40 thereon configured so that when the proximal end is mechanically plugged into the port 38, an electrical connection is also formed therewith. Other mechanical plug or port arrangements may also be used, such as a magnetic coupler, female to male (instead of male to female), etc.

Figure 7:
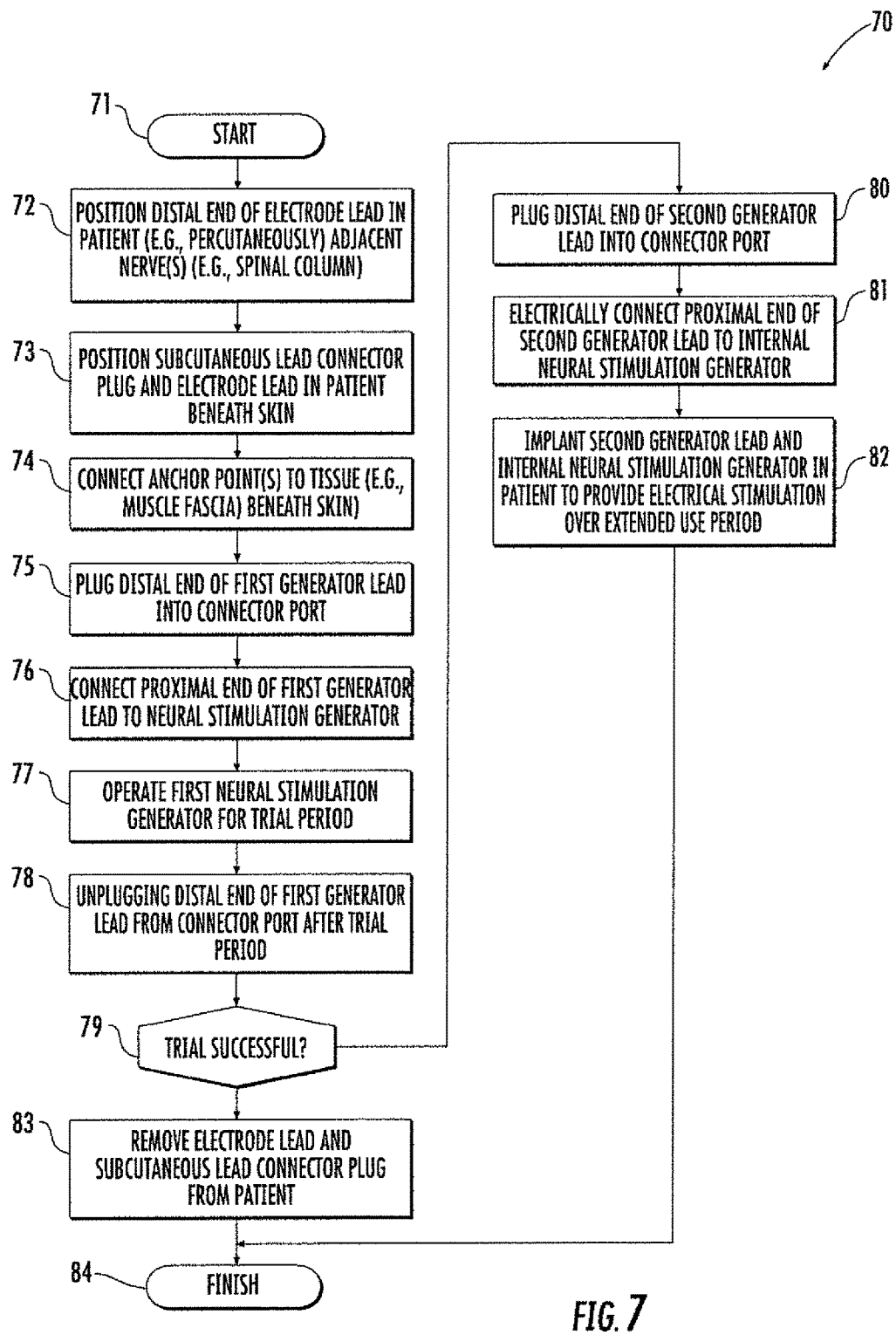
FIG. 7 is a flow diagram illustrating a neural stimulation method in accordance with an example embodiment.

Referring additionally to the flow diagram 70 of FIG. 7, beginning at Block 71, in one example implementation a surgeon or practitioner may percutaneously position the distal end 33 of the electrode lead 31 adjacent the spinal nerves 35 at the desired location, such as in the T12-L1 region, for example (although the distal end may be positioned adjacent other regions of the spine as well), at Block 72. The subcutaneous lead connector plug 36 may then be positioned along with the electrode lead 31 inside the patient beneath the patient's skin. In particular, the housing 37 may have one or more connection or anchor points 41 thereon, such as a plastic or metal loops or cleats which serve as attachment points to couple the housing to muscle fascia or other internal tissue to hold it securely in place within the patient, at Block 74. For example, the attachment may be made with a suture (e.g., silk suture), staple, or other suitable surgical connector, as will be appreciated by those skilled in the art. In the illustrated example, the distal end 33 of the electrode lead 31 is plugged into the port 38 of the subcutaneous lead connector plug 36, but as will be discussed further below in some embodiments the electrode 31 may be integrally formed with the subcutaneous lead connector plug 36 and inserted along therewith. Also, the proximal end 32 may first be plugged into the port 38 of the subcutaneous lead connector plug 37 before placement thereof within the patient, as will also be appreciated by those skilled in the art.

The system 30 further illustratively includes one or more generator leads 42 having a proximal end 43 and a distal end 44 configured to be removably plugged into and electrically connected with the connector port 39. Here again, the distal end 44 illustratively includes electrical contacts 45 which are electrically connected with corresponding electrical contacts within the port 39 when the distal end is mechanically plugged into the port, at Block 75. In the illustrated example, a four contact/electrode configuration is used, although other numbers of contacts and electrodes may be used in different embodiments. The proximal end 43, which may define a similar male plug end with electrodes 46 to that of the distal end 44, may be configured to plug into a corresponding port or receptacle of a neural stimulation generator 50, which in the example of FIG. 1 is an external neural stimulation generator which is to be carried outside of the patient's body during a trial period, as discussed above (Blocks 76-77). The external neural stimulation generator provides electrical stimulation to the spinal nerves 35 via the plurality of electrodes 34, to which it is electrically connected through the electrode lead 31, subcutaneous lead connector plug 36, and generator lead 42. It should be noted that the order in which the distal and proximal ends are plugged into the port 39 and generator 50 may be reversed in different embodiments.

More particularly, at the time of the trial an incision (e.g., a 1 to 1.5 inch incision in the vicinity of the L2 vertebra) may be made down to the muscle fascia under local anesthesia. At the superior edge of the incision a percutaneous spinal needle may be guided into the spinal canal/epidural space and confirmed with contrast. Next, a measurement may be made with a radio-opaque ruler from the tip of the needle to the expected location of the top of the lead (e.g., spanning the T8-T9 vertebrae in one application), and added to the needle length at entry into the muscle. This will give a relatively precise length of the catheter. Another option is to just have a shorter catheter available that is an estimate or approximation of this length, with a small amount of extra catheter length. The appropriately sized catheter is chosen and carefully guided into position using fluoroscopy. The patient may be awake and the position of the epidural lead may be tested and adjusted until some or all of the patient's areas of pain are covered by the stimulation from the electrodes 34. One or more additional epidural electrode leads 31 may be placed in the same manner, if desired.

During the trial, the initial generator lead 42 may be plugged into the connector port 39 and brought out of the patient via a spinal needle through the skin to a desired distance away (e.g., six inches or more). During the trial, the generator lead 42 will be "plugged in" but not firmly secured, e.g., via a set screw 53 (a corresponding set screw 52 may similarly be used for the proximal end 32 of the electrode lead 36 as well). Thus, at the end of the trial the initial generator lead 42 may be pulled out, leaving the subcutaneous lead connector plug 36 and epidural electrode lead 31 well anchored inside the patient.

Once the trial period is complete, the temporary external neural stimulation generator 50 may be disconnected from the proximal end 43 of the generator lead 42 (although it may also be disconnected during the trial period when the patient takes a break from stimulation), and the generator returned to the patient's doctor. Moreover, the doctor or surgeon may further unplug the distal end of the generator lead 42 from the connector port 39 and remove the generator lead from the patient, while leaving the electrode lead 31 and the subcutaneous lead connector plug 36 within the patient (Block 78), as will be discussed further below. If the trial is unsuccessful (Block 79), the incision may be reopened, suture anchors released, and everything removed, at Block 83, which illustratively concludes the method of FIG. 7 (Block 84).

However, if the trial is deemed a success based upon the results experienced by the patient, then the patient may be deemed a candidate for an implanted or internal neural stimulation generator 51, which may be considered "permanent" in the sense that it remains in the patient for an extended period of time, although such generators are typically removed from patients eventually due to age of the device, loss of efficacy, other surgical procedures being performed, etc. The installation procedure may include plugging the distal end 45 of a new generator lead 42 into the connector port 39, and electrically connecting the proximal end 46 of the generator lead to the internal neural stimulation generator 51, at Blocks 80-81. More particularly, at the time of permanent placement, the distal end 44 of the new generator lead 42 may be plugged and optionally "locked" into the female connector port 39 via the locking screw 53 (or other suitable attachment mechanism, as will be appreciated by those skilled in the art). The generator lead 31 placement may also be done with the patient awake to confirm good coverage of his/her pain at the time of final placement. The internal neural stimulation generator 51 and the new generator lead 42 may then be implanted inside of the patient's body (e.g., the internal neural stimulation generator 51 may be implanted near the patient's buttock) so that the internal neural stimulation generator provides electrical stimulation to spinal nerves 35 during an extended use period via the same well-placed electrodes 34 that provided beneficial results during the trial period, at Block 82.

Figure 5:
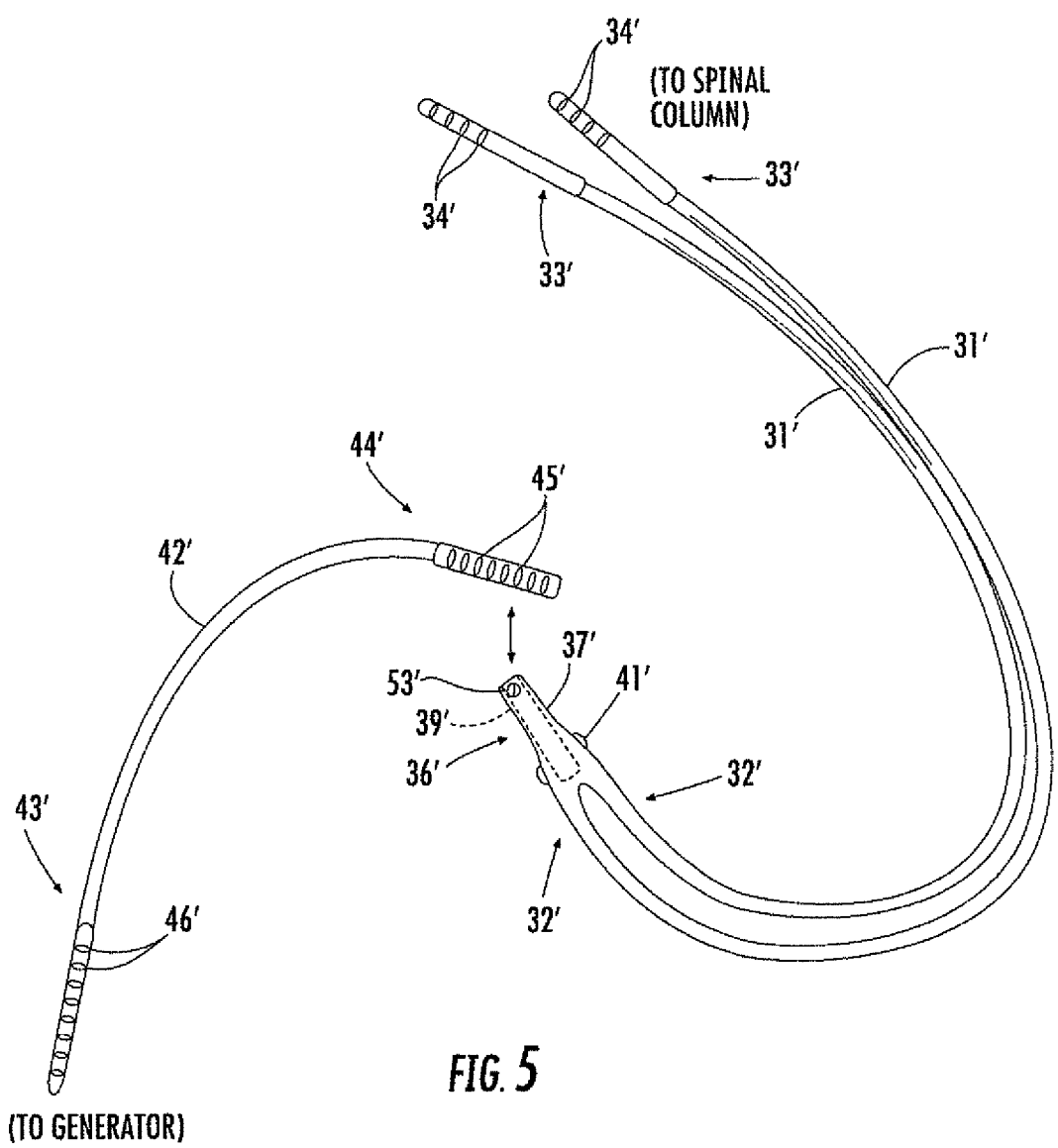
FIGS. 5 and 6 are example lead and connector arrangements in accordance with another example embodiment for use with the system of FIG. 1 before and after installation, respectively.
Figure 6:
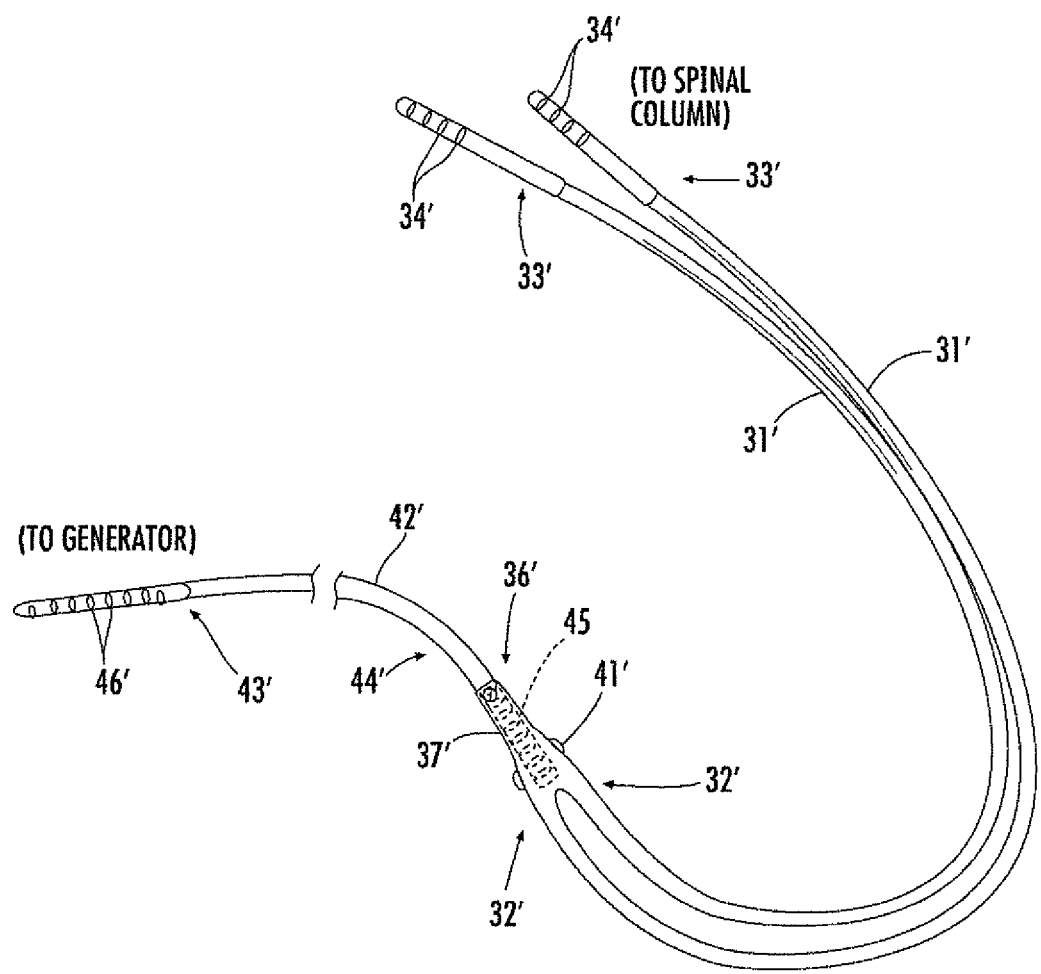

In accordance with another example approach now described with respect to FIGS. 5 and 6, the subcutaneous lead connector plug 36' and a pair of electrode leads 31' are integrally formed, meaning they are part of the same monolithic or unitary body (although other numbers of electrode leads may be used in such an embodiment). Thus, the proximal ends 32' of the epidural electrode leads 31' terminate in the housing 37' of the subcutaneous lead connector plug 36', which similarly includes a connector port 39' for the distal end 44' of the generator lead 42'. This approach may provide for a smaller subcutaneous lead connector plug to be utilized, for example. However, in some circumstances the female connector port 39' may be too big to withdraw the spinal needle. In such cases, a "breakaway" spinal needle (not shown) may be used to allow the spinal needle to be withdrawn and then split down the middle, or in multiple sections, and removed.

Another example approach would be to integrally form the housing on the distal end of the generator lead, which is removed after the trial period while the electrode lead remains in the patient until the new generator lead is connected thereto during the permanent phase. This approach and that described with respect to FIGS. 5-6 may be used with a single electrode or generator lead, or multiple electrode or generator leads may be used depending upon the given implementation. In the example of FIGS. 5-6, a respective set of four electrodes 34' is used on each of the distal ends 33' of the electrode leads 31', and thus the single generator lead has eight electrodes 46', 45' on the proximal and distal ends 43', 44', respectively for each of the leads. Other suitable electrode and/or generator lead configurations may also be used, as will be appreciated by those skilled in the art.

Many modifications and other embodiments will come to the mind of one skilled in the art having the benefit of the teachings presented in the foregoing descriptions and the associated drawings. Therefore, it is understood that various modifications and embodiments are intended to be included within the scope of the appended claims.

That which is claimed is:

1. A neural stimulation method comprising:
   using at least one electrode lead having a proximal end and a distal end and comprising a plurality of spaced apart electrodes carried by the distal end, positioning the distal end of the at least one electrode lead so that the electrodes are adjacent at least one spinal nerve in a patient through an incision at a first location;
   using a subcutaneous lead connector plug comprising a housing electrically connected to the proximal end of the at least one electrode lead and defining at least one lead connection port and at least one anchor point carried by the housing, positioning the housing along with the proximal end of the at least one electrode lead inside the patient beneath the patient's skin;

connecting the at least one anchor point to tissue beneath the patient's skin;

using a first generator lead having a distal end and a proximal end, plugging the distal end of the first generator lead into the at least one lead connector port to electrically connect the distal end of the second lead with the at least one lead connector port;

removing the proximal end of the first generator lead through the patient's skin at a second location spaced apart from the first location using a needle;

connecting the proximal end of the first generator lead to an external neural stimulation generator outside of the patient's body, and operating the first neural stimulation generator during a trial period to provide electrical stimulation to the at least one spinal nerve via the plurality of electrodes; and unplugging the distal end of the first generator lead from the at least one lead connector port after the trial period while leaving the at least one electrode lead and the subcutaneous lead connector plug inside the patient.

2. The neural stimulation method of claim 1 further comprising, after the trial period:

plugging a distal end of a second generator lead into the at least one lead connector port to provide an electrical connection therewith;

electrically connecting a proximal end of the second generator lead to an internal neural stimulation generator; and implanting the second generator lead and the internal neural stimulation generator inside of the patient's body at the second location so that the internal neural stimulation generator provides electrical stimulation to the at least one spinal nerve via the plurality of electrodes during an extended use period.

3. The neural stimulation method of claim 2 wherein the at least one lead connection port comprises a respective lead connection port for the proximal end of the at least one electrode lead, and for the distal ends of the first and second generator leads; and further comprising plugging the proximal end of the at least one electrode lead into its respective lead connection port to provide an electrical connection therewith.

4. The neural stimulation method of claim 1 wherein the at least one electrode lead and the subcutaneous lead connector plug are integrally formed.

5. The neural stimulation method of claim 1 wherein the at least one electrode lead comprises a pair of electrode leads.

6. The neural stimulation method of claim 1 wherein the at least one anchor point comprises at least one anchor loop carried by the housing; and wherein connecting the at least one anchor point comprises connecting the at least one anchor loop to tissue beneath the patient's skin.

7. The neural stimulation method of claim 1 wherein the at least one anchor point comprises a plurality of anchor points spaced apart along the housing.

8. The neural stimulation method of claim 1 wherein positioning the distal end of the at least one electrode lead comprises inserting the distal end of the at least one electrode lead percutaneously.

9. The neural stimulation method of claim 1 wherein the at least one lead connection port comprises at least one female lead connection port, and wherein the distal end of the at least one generator lead defines a corresponding male connection plug for the at least one female lead connection port.

10. The neural stimulation method of claim 1 wherein the subcutaneous lead connector plug further comprises at least one set screw carried by the housing, and further comprising securing the distal end of the at least one generator lead within the at least one lead connector port using the at least one set screw.

11. A neural stimulation method comprising:

using at least one electrode lead having a proximal end and a distal end and comprising a plurality of spaced apart electrodes carried by the distal end, positioning the distal end of the at least one electrode lead percutaneously so that the electrodes are adjacent at least one spinal nerve in a patient through an incision at a first location;

using a subcutaneous lead connector plug comprising a housing electrically connected to the proximal end of the at least one electrode lead and defining at least one lead connection port and at least one anchor point carried by the housing, positioning the housing along with the proximal end of the at least one electrode lead inside the patient beneath the patient's skin;

connecting the at least one anchor point to tissue beneath the patient's skin;

using a first generator lead having a distal end and a proximal end, plugging the distal end of the first generator lead into the at least one lead connector port to electrically connect the distal end of the second lead with the at least one lead connector port;

removing the proximal end of the first generator lead through the patient's skin at a second location spaced apart from the first location using a needle;

connecting the proximal end of the first generator lead to an external neural stimulation generator outside of the patient's body, and operating the first neural stimulation generator during a trial period to provide electrical stimulation to the at least one spinal nerve via the plurality of electrodes; and after the trial period, unplugging the distal end of the first generator lead from the at least one lead connector port while leaving the at least one electrode lead and the subcutaneous lead connector plug inside the patient, plugging a distal end of a second generator lead into the at least one lead connector port to provide an electrical connection therewith after the trial period, electrically connecting a proximal end of the second generator lead to an internal neural stimulation generator, and implanting the second generator lead and the internal neural stimulation generator inside of the patient's body at the second location so that the internal neural stimulation generator provides electrical stimulation to the at least one spinal nerve via the plurality of electrodes during an extended use period.

12. The neural stimulation method of claim 11 wherein the at least one lead connection port comprises a respective lead connection port for the proximal end of the at least one electrode lead, and for the distal ends of the first and second generator leads; and further comprising plugging the proximal end of the at least one electrode lead into its respective lead connection port to provide an electrical connection therewith.

13. The neural stimulation method of claim 11 wherein the at least one electrode lead and the subcutaneous lead connector plug are integrally formed.

14. The neural stimulation method of claim 11 wherein the at least one electrode lead comprises a pair of electrode leads.

15. The neural stimulation method of claim 11 wherein the at least one anchor point comprises at least one anchor loop carried by the housing; and wherein connecting the at least one anchor point comprises connecting the at least one anchor loop to tissue beneath the patient's skin.

16. The neural stimulation method of claim 11 wherein the at least one anchor point comprises a plurality of anchor points spaced apart along the housing.

17. The neural stimulation method of claim 11 wherein the at least one lead connection port comprises at least one female lead connection port, and wherein the distal end of the at least one generator lead defines a corresponding male connection plug for the at least one female lead connection port.

18. The neural stimulation method of claim 11 wherein the subcutaneous lead connector plug further comprises at least one set screw carried by the housing, and further comprising securing the distal end of the at least one generator lead within the at least one lead connector port using the at least one set screw.

\* \* \* \* \*